United States Patent [19]

Seng et al.

[11] 4,187,101
[45] Feb. 5, 1980

[54] 1-ACYLOXYMETHYL-4,5-DICHLORO-IMIDAZOLE DERIVATIVES AND THEIR USE AS HERBICIDES

[75] Inventors: Florin Seng; Klaus Sasse, both of Berg.Gladbach; Gunther Beck; Ludwig Eue, both of Leverkusen; Robert R. Schmidt, Cologne, all of Fed. Rep. of Germany

[73] Assignee: Bayer Aktiengeselleschaft, Leverkusen, Fed. Rep. of Germany

[21] Appl. No.: 946,252

[22] Filed: Sep. 27, 1978

Related U.S. Application Data

[62] Division of Ser. No. 835,093, Sep. 21, 1977.

[30] Foreign Application Priority Data

Oct. 13, 1976 [DE] Fed. Rep. of Germany ....... 2646142

[51] Int. Cl.² ..................... C07D 233/90; A01N 9/22
[52] U.S. Cl. .......................................... 71/92; 71/90; 71/93; 424/246; 424/248.57; 424/249; 424/250; 424/267; 424/273 R; 542/421; 544/60; 544/139; 544/182; 544/370
[58] Field of Search .................... 548/337; 424/273 R; 71/92

[56] References Cited

U.S. PATENT DOCUMENTS

| | | | |
|---|---|---|---|
| 3,423,420 | 1/1969 | Büchel et al. | 548/337 |
| 3,435,050 | 3/1969 | Wasco | 548/337 |
| 3,501,286 | 3/1970 | Draber et al. | 548/337 |
| 3,772,315 | 11/1973 | Regel et al. | 548/337 |
| 3,940,412 | 2/1976 | Pissiotas | 548/337 |
| 3,997,552 | 12/1976 | Büchel | 548/337 |

FOREIGN PATENT DOCUMENTS 1485394  5/1967  France ................................... 548/337

OTHER PUBLICATIONS

Del Corona et al., Chem. Abst. 1972, vol. 77, No. 5402g.
Shell Chem. Abst., 1966, vol. 65, Column 7187.

*Primary Examiner*—Natalie Trousof
*Attorney, Agent, or Firm*—Sprung, Felfe, Horn, Lynch & Kramer

[57] ABSTRACT

1-Acyloxymethyl-4,5-dichloro-imidazole-2-carboxylic acid derivatives of the formula

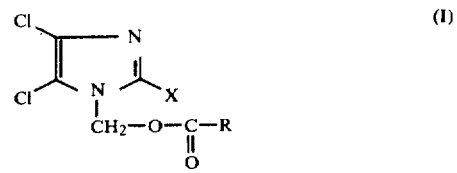

in which X represents trifluoromethyl, cyano or a group

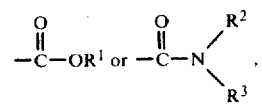

in which $R^1$ represents a saturated or unsaturated aliphatic radical, which can be carrying one or more substituents selected from halogen, alkoxy with 1 to 6 carbon atoms and alkylmercapto with 1 to 6 carbon atoms, $R^2$ represents hydrogen, alkyl with 1 to 8 carbon atoms, alkenyl with up to 8 carbon atoms or the formyl group, $R^3$ represents alkyl with 1 to 8 carbon atoms or alkenyl or alkynyl each with up to 8 carbon atoms, it being possible for each of these alkyl, alkenyl and alkynyl radicals to carry one or more substituents selected from alkoxy with 1 to 4 carbon atoms, alkylmercapto with 1 to 4 carbon atoms, phenyl (which may optionally carry one or more substituents selected from halogen, alkyl with 1 to 4 carbon atoms, trifluoromethyl and alkoxy with 1 to 4 carbon atoms), furyl or thienyl, or represents cycloalkyl with 5 to 7 carbon atoms in the ring which is optionally substituted by alkyl with 1 to 6 carbon atoms, or represents phenyl which may optionally carry one or more substituents selected from halogen, alkyl with 1 to 4 carbon atoms, alkoxy with 1 to 4 carbon atoms, alkylmercapto with 1 to 4 carbon atoms and trifluoromethyl or, $R^2$ and $R^3$ conjointly with the adjoining nitrogen atoms form an optionally substituted 5-membered to 7-membered heterocyclic ring in which 1 to 3 ring members may be selected from oxygen, sulfur and nitrogen, and R represents alkyl with 1 to 6 carbon atoms, plant protective compositions containing the same as active ingredients together with diluents, and methods for protecting plants by applying such novel 1-acyloxymethyl-4,5-dichloro-imidazole-2-carboxylic acid derivatives to a plant or its habitat.

10 Claims, No Drawings

1-ACYLOXYMETHYL-4,5-DICHLORO-IMIDAZOLE DERIVATIVES AND THEIR USE AS HERBICIDES

This is a division of application Ser. No. 835,093, filed Sept. 21, 1977.

The present invention relates to certain new 1-acyloxymethyl-4,5-dichloro-imidazole-2-carboxylic acid derivatives which possess plant protection properties, e.g., herbicidal, insecticidal, pesticidal, acaricidal and plant growth regulating properties, to a process for their preparation and to their use as plant protection agents.

It has been disclosed in Netherlands Patent Application 7,004,376 that certain benzimidazole-2-carboxylic acid derivatives possess herbicidal properties. Thus, benzimidazole-2-carboxylic acid nitrile can be employed for combating weeds. However, the activity of this substance is not always satisfactory, especially when low amounts are applied.

The present invention now provides, as new compounds, the 1-acyloxymethyl-4,5-dichloroimidazole-2-carboxylic acid derivatives of the general formula

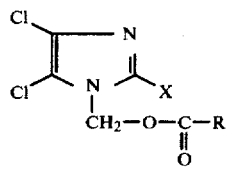

in which X represents trifluoromethyl, cyano or a group

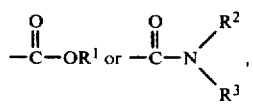

in which $R^1$ represents a saturated or unsaturated aliphatic radical, which can be carrying one or more substituents selected from halogen, alkoxy with 1 to 6 carbon atoms and alkylmercapto with 1 to 6 carbon atoms, $R^2$ represents hydrogen, alkyl with 1 to 8 carbon atoms, alkenyl with up to 8 carbon atoms or the formyl group, $R^3$ represents alkyl with 1 to 8 carbon atoms or alkenyl or alkynyl each with up to 8 carbon atoms, it being possible for each of these alkyl, alkenyl and alkynyl radicals to carry one or more substituents selected from alkoxy with 1 to 4 carbon atoms, alkylmercapto with 1 to 4 carbon atoms, phenyl (which may optionally carry one or more substituents selected from halogen, alkyl with 1 to 4 carbon atoms, trifluoromethyl and alkoxy with 1 to 4 carbon atoms), furyl or thienyl, or represents cycloalkyl with 5 to 7 carbon atoms in the ring which is optionally substituted by alkyl with 1 to 6 carbon atoms, or represents phenyl which may optionally carry one or more substituents selected from halogen, alkyl with 1 to 4 carbon atoms, alkoxy with 1 to 4 carbon atoms, alkylmercapto with 1 to 4 carbon atoms and trifluoromethyl, or $R^2$ and $R^3$ conjointly with the adjoining nitrogen atom form an optionally substituted 5-membered to 7-membered heterocyclic ring in which 1 to 3 ring members may be selected from oxygen, sulphur and nitrogen, and R represents alkyl with 1 to 6 carbon atoms.

Surprisingly, the 1-acyloxymethyl-4,5-dichloroimidazole-2-carboxylic acid derivatives according to the invention, of the formula (I), exhibit a considerably better herbicidal activity than benzimidazole-2-carboxylic acid nitrile, known from the state of the art, which is the nearest active compound of the same type of action. In addition, the compounds according to the invention are very suitable for use as plant-growth regulators and for combating insects and acarids, especially mites. Accordingly, the compounds according to the invention represent a valuable enrichment of the art.

Preferably, X represents trifluoromethyl, cyano or a group $—CO—OR^1$ or $—CO—NR^2R^3$, in which $R^1$ represents a saturated or unsaturated aliphatic radical with 1 to 6 carbon atoms, especially straight-chain or branched alkyl with 1 to 6 carbon atoms or straight-chain or branched alkenyl or alkynyl, each with up to 6 carbon atoms, which radical can carry one or more substituents selected from fluorine, chlorine, bromine, alkoxy with 1 to 4 carbon atoms and alkylmercapto with 1 to 4 carbon atoms;

$R^2$ represents hydrogen, straight-chain or branched alkyl with 1 to 6 carbon atoms, straight-chain or branched alkenyl with up to 6 carbon atoms or the formyl group;

$R^3$ represents straight-chain or branched alkyl with 1 to 6 carbon atoms or straight-chain or branched alkenyl or alkynyl each with up to 6 carbon atoms, it being possible for each of these radicals to carry one or more substituents selected from furyl, thienyl, alkoxy with 1 to 3 carbon atoms, alkylmercapto with 1 to 3 carbon atoms and phenyl which may itself optionally carry one or more substituents selected from fluorine, chlorine, bromine, alkyl with 1 to 3 carbon atoms, alkoxy with 1 to 3 carbon atoms and trifluoromethyl, or represents a cyclopentyl or cyclohexyl group which is optionally substituted by alkyl with 1 to 4 carbon atoms, or represents phenyl which optionally carries one or more substituents selected from fluorine, chlorine, bromine, alkyl with 1 to 3 carbon atoms, alkoxy with 1 to 3 carbon atoms, alkylmercapto with 1 to 3 carbon atoms and trifluoromethyl; or $R^2$ and $R^3$ conjointly with the adjoining nitrogen atom represent a saturated or unsaturated heterocyclic ring with 5 to 7 ring members, it being possible for the heterocyclic ring also to contain, additionally to the said nitrogen atom already mentioned, 1 or 2 further hetero-atoms selected from oxygen, sulphur and nitrogen atoms (heterocyclic radicals which may be mentioned as examples being pyrrolidinyl, piperidinyl, piperazinyl, hexamethyleneimidinyl, morpholinyl, thiamorpholinyl, 1,2,4-triazinyl and imidazolyl); and R represents straight-chain or branched alkyl with 1 to 4 carbon atoms (especially methyl, ethyl, propyl, isopropyl, butyl or isobutyl).

The present invention also provides a process for the preparation of a 1-acyloxymethyl-4,5-dichloroimidazole-2-carboxylic acid derivative of the formula (I) in which a 4,5-dichloro-imidazole-2-carboxylic acid derivative of the general formula

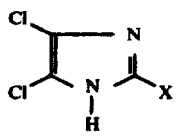

in which X has the meaning stated above, is reacted with formaldehyde or a formaldehyde donor and with a carboxylic acid anhydride of the general formula

in which R has the meaning stated above, if desired, in the presence of a diluent and if appropriate in the presence of a catalyst.

If 4,5-dichloro-imidazole-2-carboxylic acid isopropyl ester, formaldehyde and acetic anhydride are used as starting materials, the course of the reaction, in accordance with the process of the invention, can be represented by the following equation:

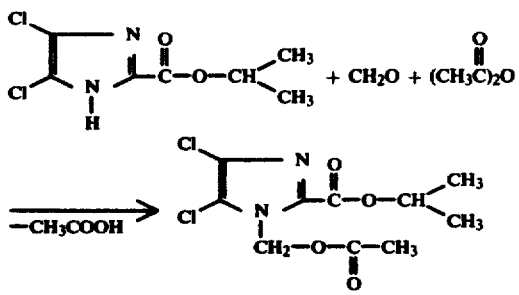

The following may be mentioned individually as examples of the 4,5-dichloro-imidazole-2-carboxylic acid derivatives of the formula (II) which may be used according to the invention: 4,5-dichloro-2-trifluoromethyl-imidazole, 4,5-dichloro-2-cyano-imidazole, 4,5-dichloro-imidazole-2-carboxylic acid methyl ester, 4,5-dichloro-imidazole-2-carboxylic acid ethyl ester, 4,5-dichloro-imidazole-2-carboxylic acid isopropyl ester, 4,5-dichloro-imidazole-2-carboxylic acid butyl ester, 4,5-dichloro-imidazole-2-carboxylic acid sec.-butyl ester, 4,5-dichloro-imidazole-2-carboxylic acid tert.-butyl ester, 4,5-dichloro-imidazole-2-carboxylic acid neopentyl ester, 4,5-dichloro-imidazole-2-carboxylic acid hexyl ester, 4,5-dichloro-imidazole-2-carboxylic acid 2-chloro-ethyl ester, 4,5-dichloro-imidazole-2-carboxylic acid 2,2,2-trichloroethyl ester, 4,5-dichloro-imidazole-2-carboxylic acid 2-methoxy-ethyl ester, 4,5-dichloro-imidazole-2-carboxylic acid 2-butoxy-ethyl ester, 4,5-dichloro-imidazole-2-carboxylic acid 2-ethylmercapto-ethyl ester, 4,5-dichloro-imidazole-2-carboxylic acid allyl ester, 4,5-dichloro-imidazole-2-carboxylic acid propargyl ester, 4,5-dichloro-imidazole-2-carboxylic acid 2-methyl-but-3-in-2-yl ester, 4,5-dichloro-imidazole-2-carboxylic acid methylamide, 4,5-dichloro-imidazole-2-carboxylic acid ethylamide, 4,5-dichloro-imidazole-2-carboxylic acid isopropylamide, 4,5-dichloro-imidazole-2-carboxylic acid sec.-butylamide, 4,5-dichloro-imidazole-2-carboxylic acid tert.-butylamide, 4,5-dichloro-imidazole-2-carboxylic acid allylamide, 4,5-dichloro-imidazole-2-carboxylic acid 2-methyl-but-3-in-2-yl amide, 4,5-dichloro-imidazole-2-carboxylic acid 2-ethoxy-ethylamide, 4,5-dichloro-imidazole-2-carboxylic acid 3-methoxy-propylamide, 4,5-dichloro-imidazole-2-carboxylic acid 2-methylmercapto-ethylamide, 4,5-dichloro-imidazole-2-carboxylic acid benzylamide, 4,5-dichloro-imidazole-2-carboxylic acid 4-chlorobenzylamide, 4,5-dichloro-imidazole-2-carboxylic acid 4-methylbenzylamide, 4,5-dichloro-imidazole-2-carboxylic acid 4-trifluoromethyl-benzylamide, 4,5-dichloro-imidazole-2-carboxylic acid 4-methoxy-benzylamide, 4,5-dichloro-imidazole-2-carboxylic acid cyclopentylamide, 4,5-dichloro-imidazole-2-carboxylic acid cyclohexylamide, 4,5-dichloro-imidazole-2-carboxylic acid anilide, 4,5-dichloro-imidazole-2-carboxylic acid 4-chloroanilide, 4,5-dichloro-imidazole-2-carboxylic acid 3,4-dichloro-anilide, 4,5-dichloro-imidazole-2-carboxylic acid 4-methylanilide, 4,5-dichloro-imidazole-2-carboxylic acid 4-methoxy-anilide, 4,5-dichloro-imidazole-2-carboxylic acid 4-chloro-3-trifluoromethyl-anilide, 4,5-dichloro-imidazole-2-carboxylic acid 2-furyl-methylamide, 4,5-dichloro-imidazole-2-carboxylic acid 2-thienylmethylamide, 4,5-dichloro-imidazole-2-carboxylic acid dimethylamide, 4,5-dichloro-imidazole-2-carboxylic acid diethylamide, 4,5-dichloro-imidazole-2-carboxylic acid diisopropylamide, 4,5-dichloro-imidazole-2-carboxylic acid N-methylbutylamide, 4,5-dichloro-imidazole-2-carboxylic acid N-methylcyclohexylamide, 4,5-dichloro-imidazole-2-carboxylic acid N-methyl-anilide, 4,5-dichloro-imidazole-2-carboxylic acid N-formylmethylamide, 4,5-dichloro-imidazole-2-carboxylic acid N-formyl-isopropylamide, 4,5-dichloro-imidazole-2-carboxylic acid pyrrolidide, 4,5-dichloro-imidazole-2-carboxylic acid piperidide, 4,5-dichloro-imidazole-2-carboxylic acid hexamethyleneimide, 4,5-dichloro-imidazole-2-carboxylic acid morpholide and 4,5-dichloro-imidazole-2-carboxylic acid thiamorpholide.

The 4,5-dichloro-imidazole-2-carboxylic acid derivatives of the formula (II) required as starting compounds have not previously been described in the literature. However, they can be prepared in a simple manner starting from 4,5-dichloro-2-dichloromethylene-imidazole of the formula (IV), 4,5-dichloro-2-trichloromethyl-imidazole of the formula (V) or the compound of the formula (VI):

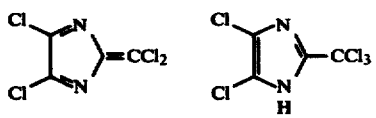

(IV)

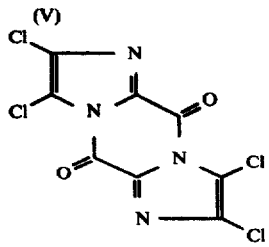

(VI).

Thus, for example, 4,5-dichloro-2-trifluoromethyl-imidazole is obtained by reacting 4,5-dichloro-2-dichloromethylene-imidazole of the formula (IV) or 4,5-dichloro-2-trichloromethyl-imidazole of the formula (V) with excess hydrogen fluoride, if desired in the presence of an inert diluent, at temperatures between 0° C. and 200° C., preferably between 20° C. and 150° C. The reaction product is isolated by stripping off the excess hydrogen fluoride after completion of the reaction, dissolving the residue in tetrahydrofuran, adding sodium fluoride and then filtering and distilling the mixture.

Expressed in terms of formulas, the course of this reaction can be illustrated as follows:

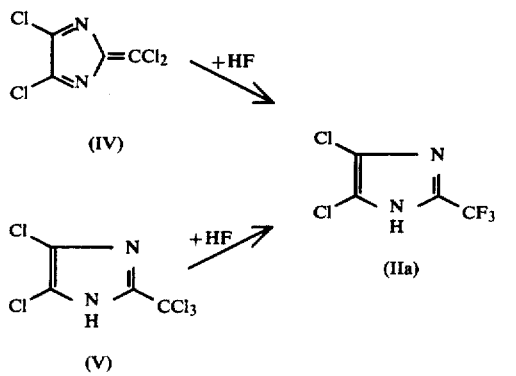

4,5-Dichloro-2-cyano-imidazole can be prepared by reacting 4,5-dichloro-2-trichloromethyl-imidazole of the formula (V) with excess ammonia, if desired in the presence of a diluent, such as, for example, dioxane, tetrahydrofuran or ethanol, at temperatures between −20° C. and +50° C. Working up is effected by filtering off the insoluble constituents after completion of the reaction, evaporating the filtrate, dissolving the combined residues in hot water and precipitating the product by acidifying with dilute mineral acid.

Expressed in terms of formulas, the course of this reaction can be illustrated as follows:

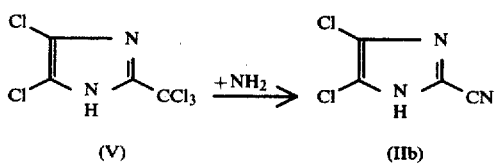

Those compounds of the formula (II) in which X represents the

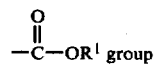

can be prepared by reacting 4,5-dichloro-2-dichloromethylene-imidazole of the formula (IV) or 4,5-dichloro-2-trichloro-methyl-imidazole of the formula (V) with alcohols of the formula $$R^1—OH \quad (VII)$$

in which $R^1$ has the meaning stated above, if desired, in the presence of an acid-binding agent, for example an alkali metal hydroxide or carbonate or alkaline earth metal hydroxide or carbonate or a tertiary amine, and, if appropriate, in the presence of an inert diluent, for example benzine gasoline, carbon tetrachloride, toluene, chlorobenzene, diethyl ether, tetrahydrofuran or dioxane, at temperatures between 0° C. and 150° C. The reaction products are in general isolated by distilling off the volatile constituents after completion of the reaction, and, if appropriate, purifying the product which thus remains, by recrystallisation.

Expressed in terms of formulas, the course of this reaction can be illustrated as follows:

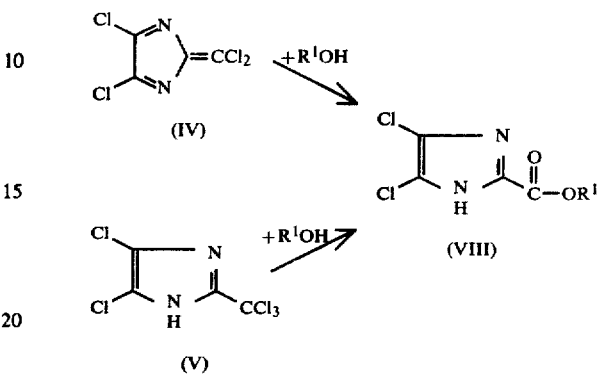

Those compounds of the formula (II), in which X represents a

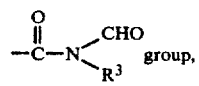

can be prepared by reacting 4,5-dichloro-2-dichloromethylene-imidazole of the formula (IV) with, per mole, at least 2 moles of a formic acid amide of the formula

in which $R^3$ has the meaning stated above, if desired in the presence of a diluent, such as, for example, an aliphatic or aromatic hydrocarbon, an open-chain or cyclic ether or an aliphatic nitrile, at temperatures between −10° C. and +110° C. The working up is effected by pouring the reaction mixture, after completion of the reaction, into ice water. Hereupon, the product precipitates in a crystalline form.

Expressed in terms of formulas, the course of this reaction can be illustrated as follows:

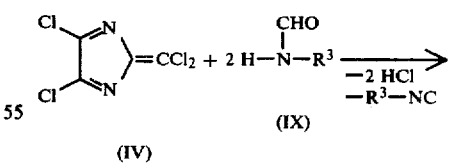

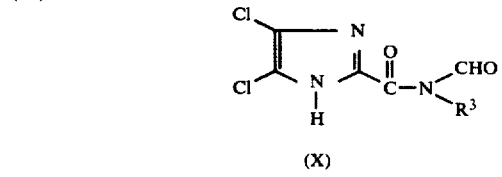

If, in the reaction described above, at least 1 mole of water if furthermore added per mole of 4,5-dichloro-2-dichloromethylene-imidazole of the formula (IV), a compound of the formula (II), in which $R^2$ represents hydrogen, is obtained directly, at a reaction temperature of between 50° C. and 150° C., in a one-vessel process.

Expressed in terms of formulas, the course of this reaction can be illustrated as follows:

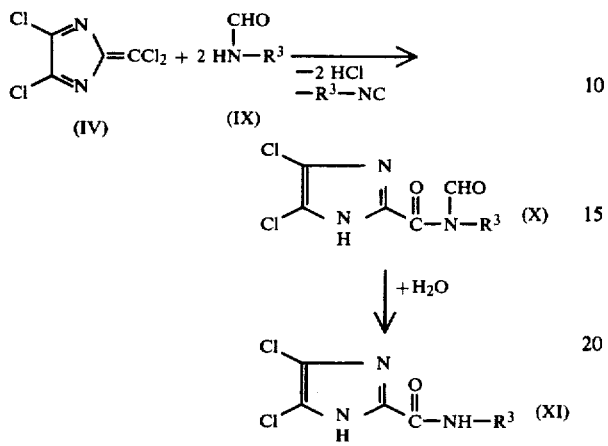

Those compounds of the formula (II), in which X represents a

 group, can be prepared by (a) reacting 4,5-dichloro-2-dichloromethylene-imidazole of the formula (IV) or 4,5-dichloro-2-trichloromethyl-imidazole of the formula (V), in a first stage, with an amine hydrochloride of the formula

 (XII)

in which $R^2$ and $R^3$ have the meanings stated above, in the presence of an aprotic solvent, such as a cyclic ether, for example tetrahydrofuran or dioxane, at temperatures between 50° C. and 200° C., and then, in a second stage, treating the resulting intermediate product, without prior isolation, with water at temperatures between 0° C. and 100° C., or by (b) reacting the compound of the formula (VI) with an amine of the formula

 (XIII)

in which $R^2$ and $R^3$ have the meanings stated above, if appropriate in the presence of a diluent, such as, for example, water, alcohol, ether, ketone, aliphatic, or aromatic hydrocarbons, dimethylformamide or dimethylsulphoxide, at temperatures between −20° C. and +120° C.

Both in the process according to variant (a) and in the process according to variant (b), working up takes place by pouring the reaction mixture, after completion of the reaction, into water, if necessary whilst cooling. Hereupon, the product is obtained in a solid form.

Expressed in terms of formulas, the course of the reactions according to process variants (a) and (b) can be illustrated as follows:

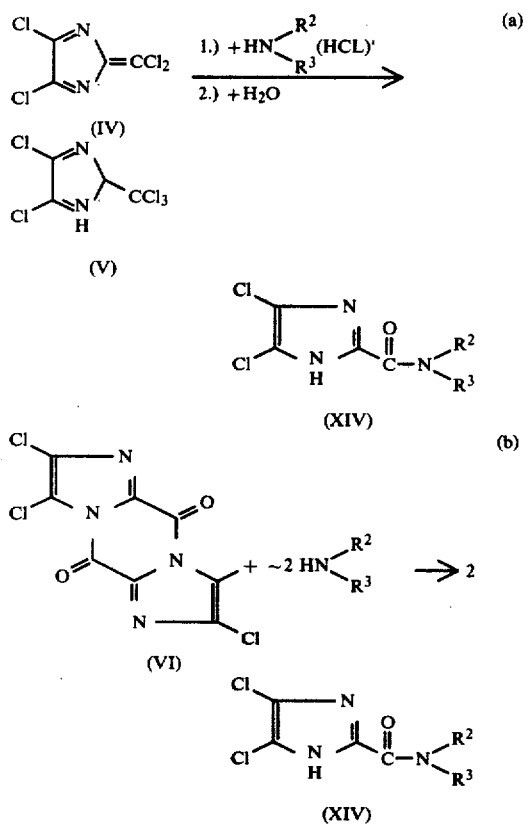

The 4,5-dichloro-2-dichloromethylene-imidazole of the formula (IV) is known and described in German Offenlegungsschrift No. 2,454,326.

The 4,5-dichloro-2-trichloromethyl-imidazole of the formula (V) has not previously been described in the literature. However, it can be prepared in a simple manner by treating 4,5-dichloro-2-dichloromethylene-imidazole of the formula (IV) with dry hydrogen chloride at temperatures between −20° C. and +100° C., if desired, in the presence of a diluent. Suitable diluents for this are all inert organic solvents, especially aliphatic or aromatic hydrocarbons or halogeno-hydrocarbons, such as, for example, benzine(gasoline), benzene, toluene, methylene, chloride, chloroform, carbon tetrachloride or chlorobenzene, and ethers such as, for example, diethyl ether, dibutyl ether, tetrahydrofuran and dioxan.

The compound of the formula

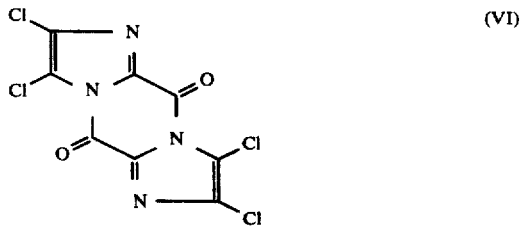 (VI)

has not previously been described in the literature. However, it can be prepared in a simple manner by treating 4,5-dichloro-2-dichloromethylene-imidazole of the formula (IV) with water at temperatures between 0° C. and 100° C.

The compounds of the formulas (VII), (IX), (XII) and (XIII) also required as starting materials in preparing the compounds of the formula (II) are known or can be prepared in accordance with processes which have already been described.

The carboxylic acid anhydrides of the formula (III) are known. Examples which may be mentioned individually are: acetic anhydride, propionic acid anhydride, butyric acid anhydride and isobutyric acid anhydride.

When carrying out the process according to the invention, formaldehyde is preferably employed in the anhydrous state in the form of the formaldehyde donors paraformaldehyde or trioxane.

When carrying out the process according to the invention, the carboxylic acid anhydride which serves as a reaction component is appropriately employed in an excess such that it acts as a solvent or diluent at the same time. However, it is also possible to carry out the reaction in the presence of another diluent. Possible diluents of this type are inert organic solvents, especially carboxylic acid nitriles, such as acetonitrile, propionitrile, adipic acid dinitrile and benzonitrile. If trioxane is used as the formaldehyde donor, this can also act as the diluent if it is employed in a sufficiently large excess.

Catalysts which can be used in the reaction according to the invention are organic sulphonic acids, such as methanesulphonic acid, benzenesulphonic acid or toluenesulphonic acid.

When carrying out the reaction by the process according to the invention, the reaction temperatures can be varied within a substantial range. In general, the reaction is carried out at a temperature of from 30° C. to 200° C. and preferably from 60° C. to 150° C.

With the process according to the invention, the reaction is generally carried out under normal pressure. However, it is also possible to carry out the reactions in a closed vessel under the particular autogenous pressure of the reactants or of the diluent.

When carrying out the process according to the invention, at least 1 mole of formaldehyde, or a corresponding amount of a formaldehyde donor, and, where appropriate, 0.01 to 0.1 mole of a catalyst are employed per mole of the 4,5-dichloro-imidazole-2-carboxylic acid derivative of the formula (II). The reaction products may be isolated according to customary methods. In general, the procedure is that, after the reaction has ended, any solvent which may be present, and also excess carboxylic acid anhydride, or the acid formed therefrom, are distilled off and the residue is either converted into the crystalline state by treatment with a suitable solvent or is taken up in a solvent, after which the solution is filtered and the filtrate distilled.

Examples which may be mentioned individually of the 1-acyloxymethyl-4,5-dichloroimidazole-2-carboxylic acid derivatives according to the invention are: 1-acetoxymethyl-4,5-dichloro-2-trifluoromethyl-imidazole, 1-acetoxymethyl-4,5-dichloro-2-cyano-imidazole, 1-acetoxymethyl-4,5-dichloro-imidazole-2-carboxylic acid methyl ester, 1-acetoxymethyl-4,5-dichloro-imidazole-2-carboxylic acid ethyl ester, 1-acetoxymethyl-4,5-dichloro-imidazole-2-carboxylic acid isopropyl ester, 1-acetoxymethyl-4,5-dichloro-imidazole-2-carboxylic acid tert.butyl ester, 1-acetoxymethyl-4,5-dichloro-imidazole-2-carboxylic acid 2-methoxyethyl ester, 1-acetoxymethyl-4,5-dichloro-imidazole-2-carboxylic acid 2-chloroethyl ester, 1-acetoxymethyl-4,5-dichloro-imidazole-2-carboxylic acid allyl ester, 1-acetoxymethyl-4,5-dichloro-imidazole-2-carboxylic acid propargyl ester, 1-acetoxymethyl-4,5-dichloro-imidazole-2-carboxylic acid methylamide, 1-acetoxymethyl-4,5-dichloro-imidazole-2-carboxylic acid isopropylamide, 1-acetoxymethyl-4,5-dichloro-imidazole-2-carboxylic acid tert.butylamide, 1-acetoxymethyl-4,5-dichloro-imidazole-2-carboxylic acid allylamide, 1-acetoxymethyl-4,5-dichloro-imidazole-2-carboxylic acid 2-methylbut-3-in-2-yl amide, 1-acetoxymethyl-4,5-dichloro-imidazole-2-carboxylic acid 2-ethoxy-ethylamide, 1-acetoxymethyl-4,5-dichloro-imidazole-2-carboxylic acid benzylamide, 1-acetoxymethyl-4,5-dichloro-imidazole-2-carboxylic acid 4-chlorobenzylamide, 1-acetoxymethyl-4,5-dichloro-imidazole-2-carboxylic acid cyclopentylamide, 1-acetoxymethyl-4,5-dichloro-imidazole-2-carboxylic acid cyclohexylamide, 1-acetoxymethyl-4,5-dichloro-imidazole-2-carboxylic acid anilide, 1-acetoxymethyl-4,5-dichloro-imidazole-2-carboxylic acid 4-chloroanilide, 1-acetoxymethyl-4,5-dichloro-imidazole-2-carboxylic acid 3-trifluoromethyl-anilide, 1-acetoxymethyl-4,5-dichloro-imidazole-2-carboxylic acid dimethylamide, 1-acetoxymethyl-4,5-dichloro-imidazole-2-carboxylic acid diethylamide, 1-acetoxymethyl-4,5-dichloro-imidazole-2-carboxyic acid N-methyl-cyclohexylamide, 1-acetoxymethyl-4,5-dichloro-imidazole-2-carboxylic acid N-formyl-isopropylamide, 1-acetoxymethyl-4,5-dichloro-imidazole-2-carboxylic acid piperidide, 1-acetoxymethyl-4,5-dichloro-imidazole-2-carboxylic acid hexamethyleneimide, 1-acetoxymethyl-4,5-dichloro-imidazole-2-carboxylic acid morpholide, 1-propionyloxymethyl-4,5-dichloro-2-trifluoromethyl-imidazole, 1-isobutyroxymethyl-4,5-dichloro-2-trifluoromethyl-imidazole and 1-butyroxymethyl-4,5-dichloro-2-trifluoromethyl-imidazole.

As already mentioned, the compounds according to the invention can be used as plant protection agents. Above all, they are suitable for use as herbicides and plant growth regulators. In addition, they can also be employed for combating insects and acarids, especially mites.

The active compounds according to the invention influence plant growth and can therefore be used as defoliants, desiccants, agents for destroying broad-leaved plants and grasses, germination inhibitors and, especially, weedkillers. Whether the compounds according to the invention act as total herbicides or selective herbicides depends essentially on the amount used.

By "weeds" in the broadest sense there are meant plants growing in locations where they are not desired.

The active compounds according to the present invention may be used, for example, to combat the following plants:

dicotyledon weeds such as mustard (Sinapis), cress (Lepidium), bed straw (Galium), chickweed (Stellaria), camomile (Matricaria), mayweed (Anthemis), gallant soldier (Galinsoga), goosefoot (Chenopodium), annual nettle (Urtica), groundsel (Senecio), pigweed (Amaranthus), purslane (Portulaca), cocklebur (Xanthium), bindweed (Convolvulus), morning glory (Ipomoea), knotweed (Polygonum), sesbania (Sesbania), ragweed (Ambrosia), spear thistle (Cirsium), common thistle (Carduus), sow thistle (Sonchus), field cress (Rorippa), toothcup (Rotala), false pimpernel (Lindernia), deadnettle (Lamium), speedwell (Veronica), mallow (Abutilon), emex (Emex), thornapple (Datura), violet (Viola), hemp-nettle (Galeopsis), poppy (Papaver) and knapweed (Centaurea); and monocotyledon weeds such as barnyard grass (Echinochloa), foxtail (Setaria), wild millet (Panicum), crabgrass (Digitaria), timothy (Phleum), bluegrass (Poa) fescue (Festuca), goosegrass (Eleusine), signalgrass (Brachiaria), ryegrass (Lolium), cheat (Bromus), oats (Avena), flatsedge (Cyperus), sorghum (Sorghum), quackgrass (Agropyron), Bermuda grass (Cynodon), Monocharia, fimbristylis (Fimbristylis), arrowhead (Sagittaria), spikerush (Eleocharis), bulrush (Scirpus), paspalum (Paspalum), Ischaemum, gooseweed (Sphenoclea), crowfoot grass (Dactyloctenium), redtop (Agrostis), meadow foxtail (Alopecurus) and silky bent-grass (Apera).

The active compounds according to the present invention may be used, for example, as selective herbicides in the following cultures:

dicotyledon cultures such as cotton (Gossypium), soya bean (Glycine), beet (Beta), carrot (Daucus), bean (Phaseolus), pea (Pisum), potato (Solanum), flax (Linum), sweet potato (Ipomoea), broad bean (Vicia), tobacco (Nicotiana), tomato (Lycopersicon), groundnut (Arachis), cabbage (Brassica), lettuce (Lactuca), cucumber (Cucumis) and marrow (Cucurbita); and monocotyledon cultures such as rice (Oryza), maize (Zea), wheat (Triticum), barley (Hordeum), oats (Avena), rye (Secale), sorghum (Sorghum), millet (Panicum), sugar cane (Saccharum), pineapple (Ananas), asparagus (Asparagus) and onion (Allium).

However, the use of the active compounds according to the invention is in no way restricted to these plants or even to the indicated genera but also embraces other plants, in the same way.

Depending on the concentration, the compounds can be used for the total combating of weeds, for example on industrial terrain and railway tracks and on paths and squares with and without trees. Equally, the compounds can be employed for combating weeds in perennial cultures, for example forestry plantings, decorative tree plantings, orchards, vineyards, citrus groves, nut orchards, banana plantations, coffee plantations, tea plantations, rubber plantations, oil palm plantations, soft fruit plantings and hopfields, and for the selective combating of weeds in annual cultures.

The active compounds according to the instant invention can be utilized, if desired, in the form of the usual formulation or compositions with conventional inert (i.e. plant compatible) herbicide or plant growth regulant diluents or extenders, i.e. diluents, carriers or extenders of the type usable in conventional pesticide formulations or compositions, e.g. conventional pesticide dispersible carrier vehicles such as gases, solutions, emulsions wettable powders, suspensions, powder dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such a fumigating cartridges, fumigating cans, fumigating coils and the like, as well as ULV cold mist and warm mist formulations.

These are prepared in known manner, for instance by extending the active compounds with conventional herbicides or plant growth regulants dispersible liquid diluent carriers and/or dispersible solid carriers optionally with the use of carrier vehicle assistants, e.g., conventional H or PGR surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons (dichlorodifluoromethane or trichlorofluoromethane) as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.), as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially other plant protection agents, such as other insecticides, acaricides, fungicides, bactericides, rodenticides and fertilizers, if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The amount of active compound used can vary within a fairly wide range. It depends essentially on the nature of the desired effect. In general, the amounts used are from 0.1 to 20 kg of active compound per hectare, preferably from 0.2 to 15 kg/ha.

The compounds according to the invention are especially suitable for the selective combating of weeds in crops of cultured plants such as cereals, cotton and maize.

They can be used both in accordance with the pre-emergence process and in accordance with the post-emergence process.

The present invention also provides a herbicidal, plant-growth regulating, insecticidal or acaricidal composition containing as active ingredient a compound of the present invention in admixture with a solid or liquified gaseous diluent or carrier or in admixture with a liquid diluent or carrier containing a surface-active agent.

The present invention also provides a method of combating weeds, insects or acarids which comprises applying to the weeds, insects or acarids, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by weeds, insects or acarids by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The herbicidal activity of the compounds of this invention is illustrated by the following biotest Examples.

In these Examples, the compounds according to the present invention are each identified by the number (given in brackets) of the corresponding preparative Example, which will be found later in this specification.

The known comparison compounds are identified as follows:

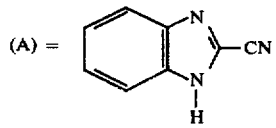

EXAMPLE A

Post-emergence Test
Solvent: 5 parts by weight of acetone
Emulsifier: 1 part by weight of alkylaryl polyglycol ether To produce a suitable preparation of active compound 1 part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way as to apply the amounts of active compound per unit area which are indicated in the table. The concentration of the spray liquor was so chosen that the amounts of active compound shown in the table were applied in 2,000 l of water/ha. After three weeks, the degree of damage to the plants was rated in % damage in comparison to the development of the untreated control. The figures denoted:
0% = no action (like untreated control)
100% = total destruction.

The active compounds, the amounts applied and the results can be seen from the table which follows:

Table A

| Active compound | Amount of active compound used kg/ha | Post emergence test | | | | | | | | | | |
|---|---|---|---|---|---|---|---|---|---|---|---|---|
| | | Echinochloa | Chenopodium | Sinapis | Calinsega | Stellaria | Urtica | Matricaria | Daucus | Oats | Cotton | Wheat |
| (1) | 1 | 90 | 100 | 100 | 100 | 100 | 100 | 100 | 100 | 100 | 0 | 100 |
| (3) | 1 | 90 | 100 | 100 | 100 | 100 | 100 | 100 | 100 | 100 | 90 | 90 |
| (4) | 1 | 100 | 100 | 100 | 100 | 100 | 100 | 100 | 100 | 100 | 60 | 0 |
| (2) | 1 | 100 | 100 | 100 | 100 | 100 | 100 | 100 | 100 | 100 | 100 | 100 |
| (7) | 1 | 80 | 100 | 100 | 100 | 100 | 100 | 100 | 100 | 20 | 100 | 20 |
| (A) | 1 | 60 | 40 | 60 | 20 | 80 | 40 | 20 | 0 | 60 | 40 | 60 |

EXAMPLE B

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:
0% = no action (like untreated control)
100% = total destruction The active compounds, the amounts applied and the results can be seen from the table which follows:

Table B

| | | Pre-emergence Test | | | | | | | | | | |
|---|---|---|---|---|---|---|---|---|---|---|---|---|
| Active compound | Amount of active compound used, kg/ha | Sina-pis | Echino-chloa | Cheno-podium | Lolium | Stella-ria | Galin-soga | Matri-caria | Oats | Cotton | Wheat | Maize |
| (1) | 5 | 100 | 100 | 100 | 100 | 100 | 100 | 100 | 100 | 20 | 100 | 100 |
| (3) | 5 | 100 | 100 | 100 | 80 | 100 | 100 | 100 | 80 | 40 | 60 | 0 |
| (4) | 5 | 100 | 90 | 100 | 80 | 100 | 100 | 100 | 60 | 20 | 40 | 0 |
| (2) | 5 | 80 | 100 | 80 | 80 | 100 | 100 | 100 | 40 | 0 | 40 | 0 |
| (7) | 5 | 100 | 80 | 100 | 80 | 100 | 100 | 100 | 90 | 0 | 60 | 0 |
| (A) | 5 | 0 | 60 | 0 | 0 | 20 | 0 | 80 | 0 | 0 | — | 0 |

PREPARATIVE EXAMPLES

EXAMPLE 1

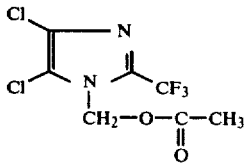
(1)

20.5 g (0.1 mol) of 4,5-dichloro-2-trifluoromethyl-imidazole were boiled under reflux with 3.3 g (0.11 mol) of paraformaldehyde in 100 ml of acetic anhydride until a virtually clear solution had formed (about 10 hours). Excess acetic anhydride and the acetic acid formed were distilled off in vacuo. The oily residue was dissolved in 100 ml of wash benzine, the solution was filtered and the filtrate was evaporated in vacuo. The residue was distilled. 19 g (69% of theory) of 1-acetoxymethyl-4,5-dichloro-2-trifluoromethylimidazole were obtained as the main fraction at a boiling point of 82°–85° C./0.075 mm Hg.

EXAMPLE 2

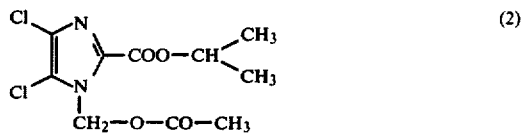
(2)

Variant a 1,392 kg (6.25 mol) of 4,5-dichloro-imidazole-2-carboxylic acid isopropyl ester were initially introduced together with 206 g (6.87 mol) of paraformaldehyde and 15 g of p-toluenesulphonic acid in 1.7 l of acetic anhydride and the mixture was stirred for 20 hours at 100° C. The excess acetic anhydride and the acetic acid formed were then distilled off under a waterpump vacuum. The residual pale oil was stirred in 100 ml of isopropanol. This gave 1,415 kg (77% of theory) of 1-acetoxymethyl-4,5-dichloro-imidazole-2-carboxylic acid isopropyl ester in the form of white crystals which, after recrystallisation from isopropanol, melted at 81°–82° C.

Analysis: $C_{10}H_{12}Cl_2N_2O_4$ (295): Calculated: C, 40.7%; H, 4.07%; N, 24.1%. Found: C, 41.1%; H, 4.2%; N, 24.1.

Variant b 44.6 g (0.2 mol) of 4,5-dichloro-imidazole-2-carboxylic acid isopropyl ester were stirred in 200 ml of acetonitrile together with 12 g (0.4 mol) of paraformaldehyde, 40.7 g (0.4 mol) of acetic anhydride and 0.5 g of p-toluenesulphonic acid for 20 hours at 85° C. After distilling off the solvent and stirring the residue in isopropanol, 38 g (64% of theory) of 1-acetoxymethyl-4,5-dichloro-imidazole-2-carboxylic acid isopropyl ester with a melting point of 81°–82° C. were obtained.

The compounds listed in Table 1 which follows were obtained by methods analogous to that described in Example 2.

| Example No. | Formula | Reaction temperature [°C.] | Reaction time [hours] | Melting point [°C.] or boiling point [°C./mm Hg] |
|---|---|---|---|---|
| 3 | Cl–/=N\\–CN, Cl–\\N/ , CH₂—O—C(=O)—CH₃ | 140 | 10 | 77–79 (wash benzine) |

| Example No. | Formula | Reaction temperature [°C.] | Reaction time [hours] | Melting point [°C.] or boiling point [°C./mm Hg] |
|---|---|---|---|---|
| 4 | Cl\C(Cl)=C/N(CH₂—O—C(=O)—C₂H₅)—N=C—CN | 140 | 10 | 140–145/0.08 |
| 5 | Cl\C(Cl)=C/N(CH₂—O—C(=O)—CH₃)—N=C—C(=O)—OCH₃ | 140 | 11 | 96–97 |
| 6 | Cl\C(Cl)=C/N(CH₂—O—C(=O)—CH₃)—N=C—C(=O)—NH—CH₃ | 140 | 5 | 130–132 |
| 7 | Cl\C(Cl)=C/N(CH₂—O—C(=O)—CH₃)—N=C—C(=O)—N(CHO)—CH(CH₃)₂ | 120 | 2 | 95–96 |

Preparation of starting materials

EXAMPLE 8

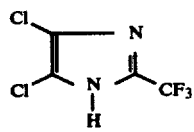

380 g (2 mol) of 4,5-dichloro-2-trichloromethyl-imidazole were initially introduced into a fluorination autoclave and 400 ml of hydrogen fluoride were added at 0° C. The autoclave was closed and a blanketing pressure of 2 atmospheres of chlorine was applied. The mixture was heated up to 100° C. in the course of 2 hours and then up to 140° C. in the course of a further 2 hours and this temperature was maintained for a further three and half hours. The pressure, which rose due to the hydrogen chloride formed, was let down by means of a condenser with the aid of a control valve set at 20 bars. After the reaction had ended, the mixture was allowed to cool, the pressure was let down and excess hydrogen fluoride was distilled off. The residue was dissolved in tetrahydrofuran; sodium fluoride was added to this solution and the mixture was shaken and filtered. After stripping off the solvent, 262 g (85.5% of theory) of 4,5-dichloro-2-trifluoromethyl-imidazole were obtained in the form of a crystalline product with a melting point of 186°–188° C.

EXAMPLE 9

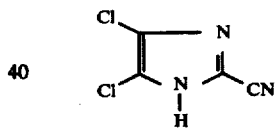

25.4 g (0.1 mol) of 4,5-dichloro-2-trichloromethyl-imidazole were introduced in small portions into 200 ml of ethanol saturated with ammonia, whilst cooling with ice and stirring vigorously. The mixture was stirred for a further 30 minutes at 50° C., the constituents which had not dissolved were then filtered off and the filtrate was evaporated under reduced pressure. The combined residues were dissolved in hot water. On acidifying the solution with dilute hydrochloric acid, the reaction product precipitated out. This was filtered off, washed with water and dried. In this way 14.6 g (90% of theory) of 4,5-dichloro-2-cyano-imidazole were obtained and after recrystallization from toluene this had a melting point of 187°–189° C.

EXAMPLE 10

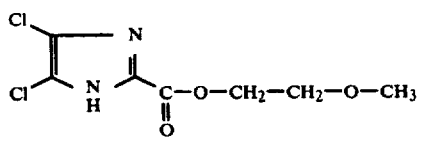

560 g (2.56 mol) of 4,5-dichloro-2-dichloromethylene-imidazole were added to 1 kg (13.2 mol) of glycol monomethyl ether, whilst cooling slightly and stirring, at such a rate that the temperature of the exothermic reaction was maintained at 80°–100° C. Thereafter the reaction mixture was evaporated to dryness in vacuo. This gave 4,5-dichloro-imidazole-2-carboxylic acid methoxy-ethyl ester in virtually quantitative yield. Melting point 130° C.

The same compound was obtained if 4,5-dichloro-2-trichloromethylimidazole was employed in place of 4,5-dichloro-2-dichloromethyleneimidazole. The reaction was carried out in the manner described above. However, it was appropriate to heat the reaction mixture to 90°–100° C. for a while after the addition of the 4,5-dichloro-2-trichloromethyl-imidazole was complete.

The compounds of the general formula

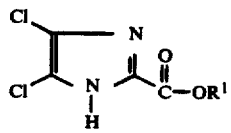
(VIII)

listed in Table 2 which follows, were obtained in an analogous manner:

Table 2

| Example No. | R¹ | Melting point (°C.) |
|---|---|---|
| 11 | CH₃ | 160 |
| 12 | CH(CH₃)₂ | 168 |

EXAMPLE 13

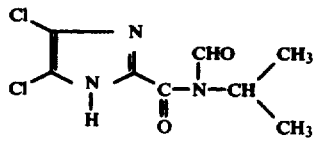

Variant (a)

654 g (3 mol) of 4,5-dichloro-2-dichloromethylene-imidazole in a finely powdered form were added, in portions, in the course of about one hour to a mixture, which had been initially introduced, of 783 g (9 mol) of isopropylformamide, 162 g (9 mol) of water and 3 liters of acetonitrile, at 0° C., whilst stirring and whilst cooling. The clear solution was then poured into 15 kg of ice water. The resulting white precipitate was filtered off, washed with water and dried. This gave 630 g (84% of theory) of 4,5-dichloro-imidazole-2-carboxylic acid N-formyl-isopropylamide with a melting point of 142° C. The same result was also obtained without the addition of water.

Variant (b)

21.8 g (0.1 mol) of 4,5-dichloro-2-dichloromethylene-imidazole in a finely powdered form were added in portions to 87 g (1 mol) of isopropyl-formamide, whilst stirring, and the reaction mixture warmed up to 40°–50° C. After the exothermic reaction had subsided, the reaction mixture was poured into excess ice water. A viscous precipitate first formed and this solidified after standing for about one hour. After the product had been filtered off, washed with water and dried, 23 g of a substance were obtained, the major part of which was identical with the product described under (a). Melting range about 132°–137° C. By fractional crystallisation from acetonitrile, it was possible, after separating off a more sparingly soluble secondary component, to isolate the product described under (a) in a pure form with a melting point of 142° C.

EXAMPLE 14

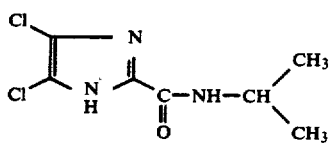

Variant (a)

From 4,5-dichloro-imidazole-2-carboxylic acid N-formylisopropylamide (see Example 10):

25 g (0.1 mol) of 4,5-dichloro-imidazole-2-carboxylic acid N-formyl-isopropylamide were stirred with 200 ml of concentrated sulphuric acid for about 15 minutes at 50°–70° C. After cooling, the reaction mixture was poured onto ice. The solid thus obtained was filtered off, washed with water until neutral and dried. This gave 16 g (72% of theory) of 4,5-dichloro-imidazole-2-carboxylic acid ispropylamide with a melting point of 150° C.

Variant (b)

From 4,5-dichloro-2-dichloromethylene-imidazole ("one-vessel process"):

654 g (3 mol) of 4,5-dichloro-2-dishloromethylene-imidazole in a finely powdered form were added in portions in the course of about one hour to a mixture, which had been initially introduced, of 783 g (9 mol) of isopropylformamide and 162 g (9 mol) of water, whilst stirring and with gentle cooling, and the internal temperature rose to about 75° C. Subsequently, the mixture was heated to about 90°–110° C. for a further half hour. After cooling, the product was precipitated in water, filtered off, washed with water and dried. This gave 566 g (85% of theory) of 4,5-dichloroimidazole-2-carboxylic acid isopropylamide with a melting point of 150° C.

EXAMPLE 15

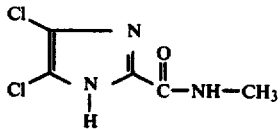

Using the method described in Example 14b, 4,5-dichloro-imidazole-2-carboxylic acid methylamide was obtained as a crystalline product with a melting point of 240° C. by reacting methyl-formamide and 4,5-dichloro-2-dichloromethylene-imidazole.

EXAMPLE 16

(V)

Dry hydrogen chloride was passed into a solution of 218 g (1.0 mol) of 4,5-dichloro-2-dichloromethyleneimidazole in about 2 liters of dry toluene until the formation of the precipitate had ceased (at least 1 mol). After cooling (the addition reaction with HCl proceeded exothermically), filtering off the product and drying, 235 g (89% of theory) of 4,5-dichloro-2-trichloromethyl-imidazole with a melting point of 210° C. (with decomposition) were obtained.

EXAMPLE 17

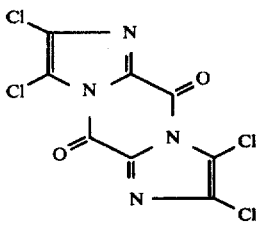
(VI)

40 g (0.55 mol) of dimethylformamide were added dropwise in the course of about 10 minutes to a boiling solution of 100 g (0.46 mol) of 4,5-dichloro-2-dichloromethyleneimidazole in 1 liter of petroleum ether (boiling range about 60° C.) and a precipitate separated out. After cooling, the petroleum ether was decanted off and the precipitate was stirred with acetone. Subsequently it was filtered off and washed with acetone until the acetone which ran off was pale yellow. This gave 41 g (55% theory) of the dimeric ketene of the above formula in the form of a pale yellow powder with a melting point of above 290° C.

What we claim is:

1. A 1-acyloxymethyl-4,5-dichloro-imidazole-2-carboxylic acid derivative of the formula

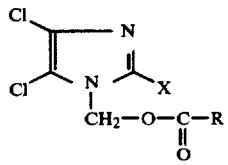
(I)

wherein
X represents trifluoromethyl or cyano and
R represents alkyl with 1 to 6 carbon atoms.

2. A 1-acyloxymethyl-4,5-dichloro-imidazole-2-carboxylic acid derivative according to claim 1 wherein R is alkyl of 1 to 4 carbon atoms.

3. The compound according to claim 1 wherein such compound is 1-acyloxymethyl-4,5-dichloro-2-trifluormethylimidazole of the formula

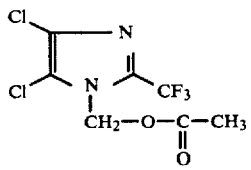
(1)

4. The compound according to claim 1 having the formula

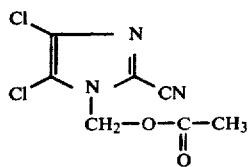

5. A compound according to claim 1 having the formula

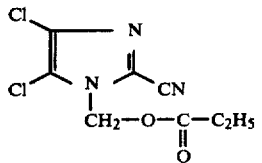

6. A composition for use as a herbicide containing as an active ingredient a herbicidally effective amount of a compound according to claim 1 in admixture with a diluent.

7. A method of combatting a weed which comprises applying to the weed or its habitat a herbicidally effective amount of a compound according to claim 1.

8. A method according to claim 7 which comprises applying said 1-acyloxymethyl-4,5-dichloro-imidazole-2-carboxylic acid derivative to the habitat of a weed prior to emergence of said weed.

9. A method according to claim 8 wherein the 1-acyloxymethyl-4,5-dichloro-imidazole-2-carboxylic acid derivative is applied to a field containing a plant which plant is selected from the group consisting of oats, cotton, wheat and maize.

10. A method according to claim 7 wherein said 1-acyloxymethyl-4,5-dichloro-imidazole-2-carboxylic acid derivative is a compound of the formula

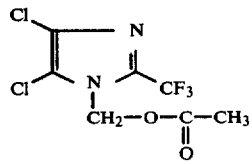

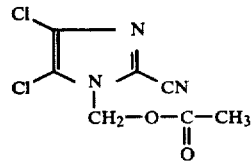

or

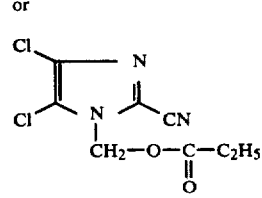

* * * * *